United States Patent [19]
McIntyre

[11] Patent Number: 5,338,298
[45] Date of Patent: Aug. 16, 1994

[54] DOUBLE-TAPERED BALLOON

[75] Inventor: Jon T. McIntyre, Lowell, Mass.

[73] Assignee: C.R. Bard, Inc., Murray Hill, N.J.

[21] Appl. No.: 71,481

[22] Filed: Jun. 4, 1993

[51] Int. Cl.$^5$ ............................................. A61M 29/00
[52] U.S. Cl. ..................................... 604/96; 604/265; 606/194
[58] Field of Search ............................... 606/192, 194; 604/96.265

[56] References Cited

U.S. PATENT DOCUMENTS

| | | | |
|---|---|---|---|
| 4,024,873 | 5/1977 | Antoshkiw et al. | 128/349 |
| 4,154,244 | 5/1979 | Becker et al. | 128/349 |
| 4,351,341 | 9/1982 | Goldberg et al. | 128/349 |
| 4,413,989 | 11/1983 | Schjeldahl et al. | 604/96 |
| 4,456,000 | 6/1984 | Schjeldahl et al. | 128/1 |
| 4,564,014 | 1/1986 | Fogarty et al. | 128/344 |
| 4,608,984 | 9/1986 | Fogarty | 128/344 |
| 4,762,129 | 8/1988 | Bonzel | 128/344 |
| 4,777,951 | 10/1988 | Cribier et al. | 128/344 |
| 4,782,834 | 11/1988 | Maguire et al. | 128/344 |
| 4,787,388 | 11/1988 | Hofmann | 128/344 |
| 4,819,751 | 4/1989 | Shimada et al. | 128/344 |
| 4,820,261 | 4/1989 | Schmoll et al. | 604/4 |
| 4,820,349 | 4/1989 | Saab | 128/344 |
| 4,881,547 | 11/1989 | Danforth | 128/344 |
| 4,896,670 | 1/1990 | Crittenden | 606/194 |
| 4,917,088 | 4/1990 | Crittenden | 606/194 |
| 4,917,666 | 4/1990 | Solar et al. | 604/95 |
| 4,955,895 | 9/1990 | Sugiyama et al. | 606/194 |
| 4,964,853 | 10/1990 | Sugiyama et al. | 604/96 |
| 4,994,032 | 2/1991 | Sugiyama et al. | 604/96 |
| 4,998,923 | 3/1991 | Samson et al. | 606/194 |
| 5,032,113 | 7/1991 | Burns | 604/96 |
| 5,041,125 | 8/1991 | Montano, Jr. | 606/192 |
| 5,049,132 | 9/1991 | Shaffer et al. | 604/101 |
| 5,078,725 | 1/1992 | Enderle et al. | 606/193 |
| 5,085,636 | 2/1992 | Burns | 604/99 |
| 5,087,246 | 2/1992 | Smith | 604/96 |
| 5,108,414 | 4/1992 | Enderle et al. | 606/193 |
| 5,226,887 | 7/1993 | Farr et al. | 604/96 |

OTHER PUBLICATIONS

Webster's New World Dictionary, Third College Edition.

*Primary Examiner*—John D. Yasko
*Assistant Examiner*—Corrine Maglione
*Attorney, Agent, or Firm*—Morgan & Finnegan

[57] ABSTRACT

A balloon dilatation catheter including a catheter shaft having a proximal end and a distal end with an inflatable balloon secured thereto. The balloon has a cylindrical section having a first end, a first tapered section of the balloon gradually tapering from a first end adjacent the first end of the cylindrical section to a second end, and a second tapered section adjacent the first tapered section. The second tapered section tapers from a primary end adjacent the second end of the first tapered section to a secondary end. The first tapered section has a first taper angle with respect to the catheter shaft and the second tapered section has a second taper angle with respect to the catheter shaft, the first taper angle being smaller than the second taper angle.

8 Claims, 2 Drawing Sheets

DOUBLE-TAPERED BALLOON

BACKGROUND OF THE INVENTION

This invention relates to catheters, and in particular to dilatation balloon catheters, for use in performance of percutaneous transluminal procedures including angioplasty.

Dilatation balloons currently used in percutaneous transluminal procedures have balloon working areas that are cylindrical in shape and whose diameter is substantially uniform throughout its working length. Such balloons typically have a working length of 20 mm. In certain circumstances, however, such dilatation balloons exhibit unacceptable performance characteristics. In particular, as shown in FIG. 4, when a standard dilatation balloon 42 is inserted and inflated in curved vascular segments, they tend to straighten the vascular walls 44. Additionally, as shown in FIG. 5, when a conventional dilatation balloon 52 is inflated in a lesion 54, the balloon can overdialate the vascular segments 56 adjacent to the lesion, particularly at high inflation pressures.

As a result, the use of "short" dilatation balloons has been attempted. Clinical experience with shorter balloon working lengths, e.g., 12 mm length PVC balloons, was expected to facilitate dilating lesions on vascular bends and discrete lesions. However, these short dilatation balloons tended to "squirt" out of the lesion upon inflation easier than standard length dilatation balloons.

Accordingly, there is a need in the art for dilatation balloons suitable for dilatation of lesions in curved arterial segments and discrete lesions.

SUMMARY OF THE INVENTION

With the foregoing in mind, it is an object of the invention to provide a dilatation balloon catheter which has improved performance characteristics as compared to conventional dilatation balloon catheters.

The dilatation balloon catheter according to the invention includes a short central cylindrical section that has a tapered section on either or both sides of the working length of the balloon. These tapered sections have a gradual reduction in diameter in comparison to the abrupt angular transition of conventional dilatation balloon ends. The dilatation balloon according to the invention provides significant advantages over conventional dilatation balloons in that it does not tend to straighten curved vascular segments when inflated. Further, the dilatation balloon according to the invention does not overdilate vascular tissue adjacent to the focal point of a discrete lesion while still imparting radial expansion in those areas.

The dilatation balloon according to the invention provides further advantages over simple short balloons because the dilating capability of the balloon does not abruptly terminate at the end of the balloon working area in somewhat diffuse lesions. In addition, the dilatation balloon according to the invention does not tend to "squirt" out of focal point lesions because upon balloon inflation the tapered sections are filled first and anchor the balloon before the central cylindrical section of the balloon is filled to dilate the lesion.

Arterial applications of the dilatation balloon according to the invention include coronary, peripheral vascular and cerebral vascular. The balloon catheter can also be used in the dilatation of structures occurring in anatomical locations other than arterial such as esophageal and urological applications.

BRIEF DESCRIPTION OF THE DRAWINGS

The accompanying drawings, referred to herein and constituting a part hereof, illustrate preferred embodiments of the invention and, together with the description, serve to explain the principles of the invention, wherein.

DETAILED DESCRIPTION OF THE DRAWINGS

Figure 1:
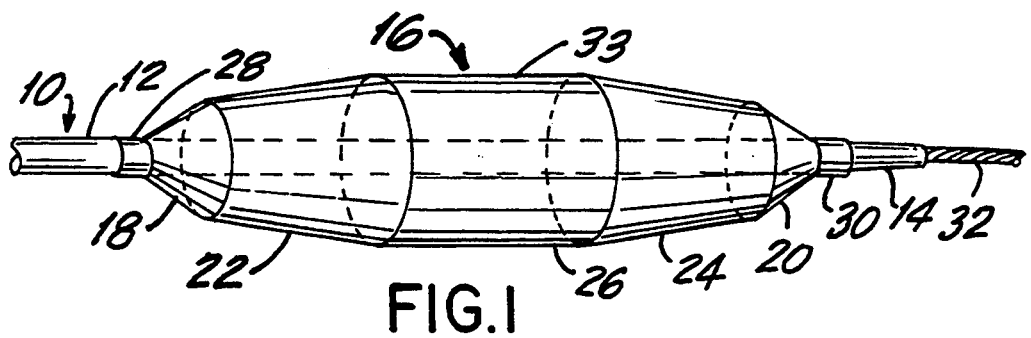
FIG. 1 is a fragmented illustration of the balloon catheter according to the invention.

As shown in FIG. 1, the balloon catheter according to the invention includes an elongate flexible shaft 10 having a proximally extending portion 12, seen to the left in FIG. 1 and a distal portion 14, seen to the right in FIG. 1. The shaft is flexible and may be formed, as by extrusion, from an appropriate plastic material such as a PVC, nylon, or polyurethane material, and, preferably, polyethylene. The shaft has at least one, and may have two or more lumens, extending longitudinally through shaft 10.

A flexible balloon, indicated generally at 16, is mounted at distal end of catheter shaft 10. The balloon is inflatable and deflatable as will be described hereinafter. The balloon 16 is formed preferably from a relatively inelastic material, such as polyethylene terephtalate (PET) or nylon. Additional balloon materials include polyurethane, polyethylene, ionomer (such as DuPont surlyn), and polyvinylchloride. The balloon may be manufactured as described in U.S. Pat. No. 4,490,421 to Levy to which reference is made and is hereby incorporated by reference. The balloon is formed to include a proximal cone section 18, a distal cone section 20, a proximal tapered section 22, a distal tapered section 24 and an intermediate cylindrical section 26. The proximal end of the proximal cone section 18 terminates in a cylindrical proximal collar 28 and the distal end of the distal cone section 20 terminates in a cylindrical distal collar 30. The balloon 16 may be attached to the catheter shaft 10 by adhesively attaching the collars 28, 30, which are 0.000354–0.001062 mm larger in diameter, to the catheter shaft.

As preferably embodied, the central cylindrical section, which forms the working length of the dilatation balloon, has a substantially uniform diameter along its length. The central cylindrical section 26 has a working length that is shorter than the working length commonly found in balloon catheters. Specifically, the central cylindrical section 26 is from 8 to 12 mm in length, while the furthest ends of the tapered sections 22, 24 are 20 to 25 mm apart. These tapered sections can also be as far as 80 mm apart. The diameter of the central cylindrical section should be from 1.5 mm to 4 mm depending upon the lesion to be dilated. The diameter may be as small as 1.0 mm and as large as 6.0 mm.

A single tapered section may be positioned on either side of the central cylindrical section or, prefereably, a pair of tapered sections from 4 to 8.5 mm in length may be positioned on both sides of the central cylindrical section. Each such tapered section tapers down uniformly as it extends away from the central cylindrical section to a diameter approximately 0.25 mm less than the diameter of the central cylindrical section.

One of the lumens in shaft 10 is used for inflating and deflating the balloon and is plugged at its distal end. An opening is provided in the shaft within the balloon 16 to communicate the inflation lumen with the interior of the balloon. An inflation medium, such as a contrast fluid visible under flouroscopy, is used to inflate and deflate the balloon and is introduced into the lumen at the proximal end of the catheter. Another lumen in shaft 10 may be provided for use of a guidewire 32 with the balloon catheter.

It is desirable that under some circumstances the dilatation balloon be able to collapse to a relatively low profile, that is, to have a relatively small effective diameter when the balloon is collapsed. To that end, the balloon may be formed so that when it is collapsed, by applying negative pressure to the balloon lumen, the balloon will tend to collapse in a pleated configuration. The balloon may be manufactured by a process that will cause the balloon to tend to collapse into the pleated configuration. In that process, after the balloon has been formed, the balloon then is tensioned by its ends until it forms a plurality of pleats while under tension. While maintaining the balloon under tension, the balloon first is heated and then cooled. The tension then may be released and the balloon thereafter will tend to assume the pleated configuration when it is collapsed. The process for forming the pleats is described in further detail in U.S. Pat. No. 5,087,246 to Smith to which reference is made and which is hereby incorporated by reference.

The dilatation balloon described herein may also be provided with a protective lubricious coating 33. A coating solution may be used which contains a protective compound such as a urethane, a slip additive such as a siloxane, and optionally, a crosslinking agent for the protective compound such as polyfunctional aziridine. The resulting surface coating is lubricous, tough and flexible. The method for providing such a coating is described in further detail in U.S. Pat. No. 5,026,607 to Kiezulas to which reference is made and which is hereby incorporated by reference.

It may be appreciated that many dilatation balloons with working segments of approximately the same length as that of the balloon described herein are prone to squirt out of the focal point of the lesion when the balloon is inflated. Advantageously, the dilatation balloon according to the invention overcomes this problem because the tapered segments of the dilatation balloon fully inflate before the central cylindrical segment and serve to hold the balloon in position. The tapered segments inherently inflate before the working segment because the lesions within the vessel apply pressure to the working segment and thus the fluid pressure is initially directed to the tapered segments.

Figure 2:
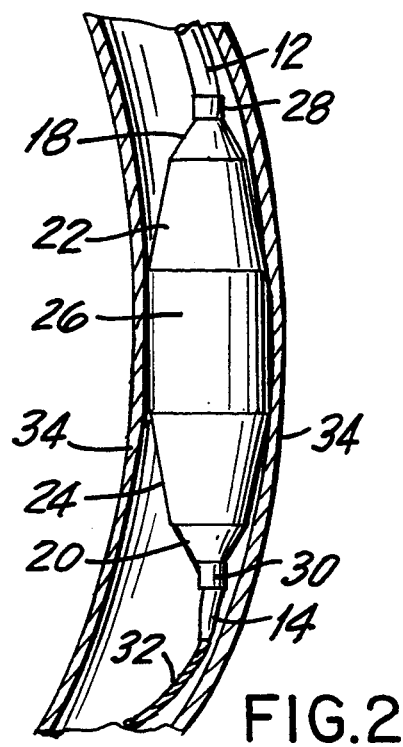
FIG. 2 is a fragmented illustration of the balloon catheter of FIG. 1 inflated in a curved artery segment.
Figure 4:
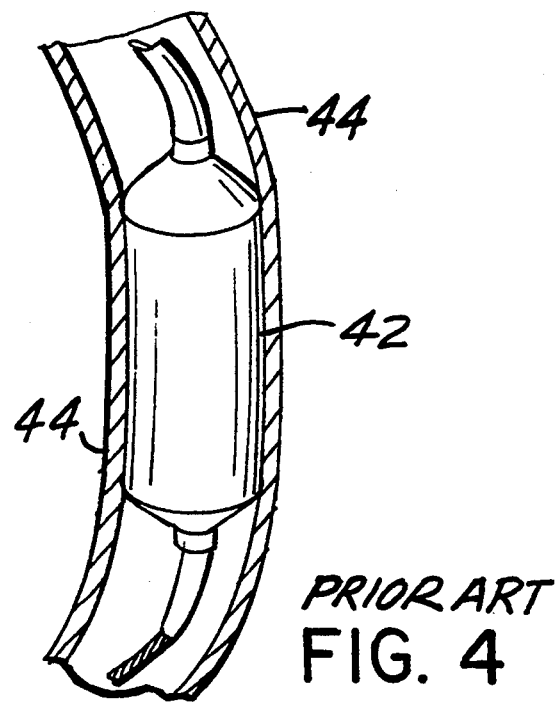
FIG. 4 is a fragmented illustration of a prior art balloon catheter inflated in a curved artery segment.

The dilatation balloon according to the invention also overcomes other problems associated with prior dilatation balloons. Specifically, as illustrated in FIG. 2, the dilatation balloon 16 has only a limited tendency to straighten curved arterial segments 34 when inflated therein as may occur with conventional balloon catheters as shown in FIG. 4.

Figure 3:
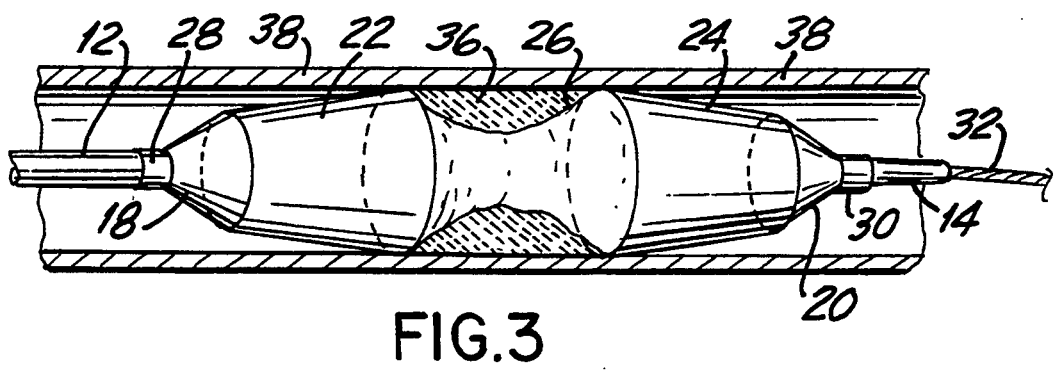
FIG. 3 is a fragmented illustration of the balloon catheter of FIG. 1 inflated in a lesion.
Figure 5:
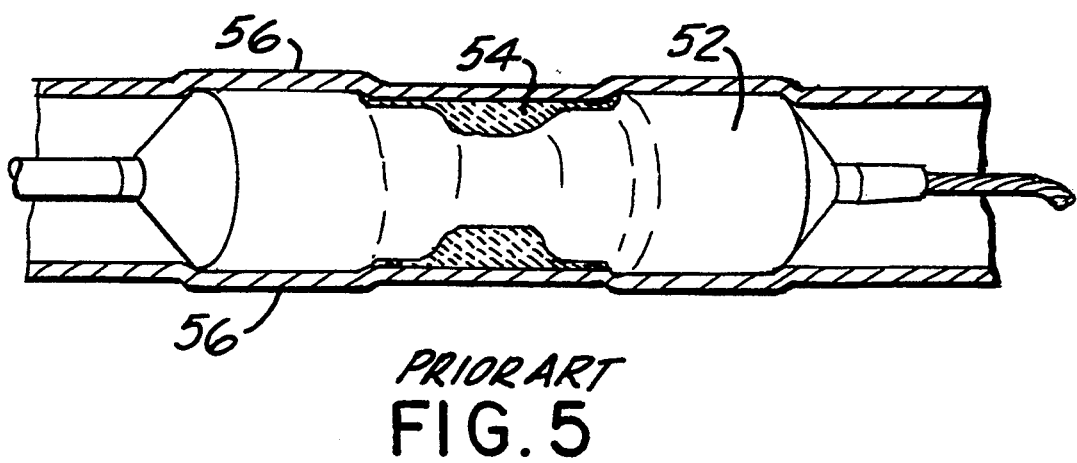
FIG. 5 is a fragmented illustration of a prior art balloon catheter inflated in a lesion.

FIG. 3 illustrates a dilatation balloon 16 inflated in a long diffuse lesion 36. The plaque adjacent to the body of the dilatation balloon is almost fully dilated, which leaves a smoother lumenal opening of the vessel upon deflation of the dilatation balloon than would be achieved with a conventional short dilatation balloon. Additionally, higher balloon inflation pressures could be achieved without risk of overdilating the vascular segments 38 as may occur with conventional balloon catheters as shown in FIG. 5.

While the invention has been described in its preferred embodiments, it is to be understood that the words which have been used are words of description, rather than limitation, and that changes may be made within the purview of the appended claims without departing from the true scope and spirit of the invention in its broader aspects.

What is claimed:

1. A balloon dilatation catheter, comprising:
   a catheter shaft having a distal end and a proximal end;
   an inflatable balloon secured to said distal end of said catheter shaft;
   said balloon including a cylindrical section having a first end;
   a first tapered section gradually tapering from a first end adjacent said first end of said cylindrical section to a second end;
   a second tapered section adjacent said first tapered section, wherein said second tapered section tapers from a primary end adjacent said second end to a secondary end; and
   wherein said first tapered section has a first taper angle with respect to the catheter shaft and said second tapered section has a second taper angle with respect to the catheter shaft, and said first taper angle is smaller than said second taper angle; and
   wherein the length of said first tapered section is at least 33% of the length of said cylindrical section.

2. A balloon dilatation catheter according to claim 1, further comprising:
   a second end of said cylindrical section;
   a third tapered section adjacent said second end of said cylindrical section;
   said third tapered section gradually tapering from a first end adjacent said second end of said cylindrical section to a second end;
   a fourth tapered section adjacent said third tapered section, wherein said fourth tapered section tapers from a primary end adjacent said second end of said third tapered section to a secondary end; and
   wherein said third tapered section has a third taper angle with respect to the catheter shaft and said fourth tapered section has a fourth taper angle with respect to the catheter shaft, and said third taper angle is smaller than said fourth taper angle.

3. A balloon dilatation catheter in accordance with claim 2, wherein said third taper angle approximately equals said first taper angle and said fourth taper angle approximately equals said second taper angle.

4. A balloon dilatation catheter according to claim 1, wherein said balloon is adhesively attached to said catheter shaft.

5. A balloon dilatation catheter according to claim 1, wherein said balloon has a cylindrical section of between 8 and 12mm.

6. A balloon dilatation catheter according to claim 1, wherein said balloon has an overall length of between 20 and 80 mm.

7. A balloon dilatation catheter according to claim 1, further comprising a lubricious coating on said balloon.

8. A balloon dilation catheter according to claim 1, further comprising a protective coating on said balloon.

* * * * *